United States Patent [19]

Hofmann

[11] Patent Number: Plant 7,086

[45] Date of Patent: Dec. 26, 1989

[54] DISTINCT VARIETY OF GERANIUM PLANT NAMED REBECA

[75] Inventor: Christa Hofmann, Dresden, German Democratic Rep.

[73] Assignee: Oglevee Ltd., Connellsville, Pa.

[21] Appl. No.: 298,510

[22] Filed: Jan. 18, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new geranium cultivar is distinguished by its bright coral bloom atop a bushy, medium green foliage that has a distinct dark green zonation. The new cultivar has a vigorous plant habit and a good mound habit.

1 Drawing Sheet

BACKGROUND OF THE NEW PLANT

The present invention comprises a new and distinct cultivar of *Pelargonium hortorum* bailey known by the varietal name of Rebeca. The new variety was discovered in a selective breeding program by Mrs. Christa Hofmann and is a selection from the crossing of unidentified salmon colored PAC varieties of the German Democratic Republic.

The new cultivar was discovered in the year 1984 at the VEB Saatzucht Zierpflanzen Dresden, German Democratic Republic; it was first asexually reproduced by cuttings in Dresden, German Democratic Republic, and has been repeatedly asexually reproduced by cuttings over a two year period for Oglevee Associates, Inc. in Connellsville, Pa. It has also been trialed and field tested over the summers of 1987 and 1988 at Connellsville, Pa., and has been found to retain its distinctive characteristics throughout successive propagation.

The new cultivar, when grown in a greenhouse in Connellsville, Pa., using natural light, 60° F. night temperature, 68° F. day temperature, and 71° F. vent temperature, has a response time of eight weeks from a well-rooted cutting to a flowering plant in a four inch (10 cm) pot.

DESCRIPTION OF THE DRAWING

The accompanying photographic drawing illustrates a new cultivar, the color being as nearly true as possible with color illustrations of this type.

DESCRIPTION OF THE NEW PLANT

The following detailed descriptions set forth the characteristics of the new cultivar. The data which defines these characteristics were collected from asexual reproductions carried out for Oglevee Associates, Inc., in Connellsville, Pa. The plant history was taken on eight-week plants in which rooting cuttings were potted Aug. 4, 1987 and subsequently flowered on Sept. 20, 1987. The plants were blossomed under natural light in a greenhouse and color readings were taken under 200–220 foot candles of cool, white fluorescent light. The cuttings were grown in a soilless media and received constant fertilizer of 250–275 parts per million nitrogen and potassium. Color references are primarily to the R.H.S. Colour Chart of The Royal Horticultural Society of London.

THE PLANT

Classification:

*Botanical.*—*Pelargonium* × *hortorum* bailey.

*Commercial.*—Zonal geranium.

Form: Bush; basal branching, free and early flowering, upright habit.

Height: 25.0–30.0 cm from the media surface.

Growth: Free-branching from base; medium internode length.

Strength: Stands upright without artificial support.

Foliage: Large leaves with strong zonation pattern.

Leaves: Leaf description is of a mature fully expanded leaf at least 4 nodes below the apical meristem.

*Size.*—8.0–15.0 cm wide.

*Shape.*—Reniform, cordate base.

*Margin.*—Crenate.

*Texture.*—Downy; dull (not reflective).

*Color.*—Outside margin: Green group 137B.

*Zonation.*—Center: Green group 137C.

*Ribs and veins.*—Palmate veination: Yellow-green group 145B.

Petioles: Stalked petiole 7.0–12.0 cm, Green group 138B.

Stem: Color: Green group 137C. Internodes: The internode length between mature leaves is 3.0–4.0 cm.

THE BUD

The umbel contains 25–45 flower buds. There are three groups of bud development on an influorescent with no open florets. The first group contains the youngest buds which are completely enclosed by the sepals. The sepals are Yellow-green group 144B. The second group appears when creamy white petals start to protrude from the sepals, Yellow-white group 158B. The third group appears in streaks in the petals and matures into solid color Red group 41A.

INFLORESCENCE

Blooming habit: Continuous, upright, semi-double, hemispherical in shape.

Size: 9.0–15.0 cm across.

Borne: Umbel; florets on pedicel, pedicel on peduncle, 4.0–8.0 cm. above foliage.

Tonality from a distance: Bright coral bloom on a bushy, medium green foliage.

Florets:

*Form.*—Flat to slightly cupped; with petaloids; obovate.

*Color.*—Top — Outer edge Red Group 43C, inner Red Group 43B. Bottom — Red Group 43C on outer edge, fading to Red Group 43D.

*Petals.*—5–8 separate-not united; margin entire obovate; palmate veination; smooth; flat to slightly cupped.

*Size.*—5.0 cm in width.

*Texture and appearance.*—Smooth surface.

Petaloids:

*Quantity.*—3–6.

*Shape.*—Narrow, elongated, twisted.

*Color.*—Top — Red group 41A. Bottom — Red group 50B.

*Length.*—3.0–4.0 cm.

*Color.*—Apical end, Red group 53A; Basal end, Green group 137C.

Peduncle: Arises from node; opposite leaf petiole; 14.0–18.0 cm. in length, Yellow-green group 146C.

REPRODUCTIVE ORGANS

Stamens:

*Anthers.*—Elliptical 1.0–2.0 mm.

*Filaments.*—White at base — coloring toward tip same as center of floret; irregular in shape; same petaloid; flat at base and twisted at tip; 5.0–7.0 mm in length.

*Pollen.*—Golden brown initially; later turns dark brown.

Pistils:

*Number.*—1 with 5 parted stigma.

*Length.*—0.5–0.9 cm in length.

*Stigma.*—5 parted; colored same as floret.

*Style.*—1; pale red to reddish color; 2.0–3.0 mm in length.

Ovaries: 3.0–5.0 mm in length; yellow-green; very pubescent; superior.

Fruit: none observed.

The new cultivar is characterized by a very good coral bloom color with attractive foliage that has a definite dark green zone. The cultivar has a vigorous plant growth habit and larger plant size as compared to Glacier Salmon (U.S. Plant Pat. No. 5,313). The cultivar also has a good mound habit.

I claim:

1. A new and distinct variety of geranium plant characterized by a bright coral bloom color, an attractive medium green foliage with a definite dark green zone, and a vigorous plant growth as herein shown and described.

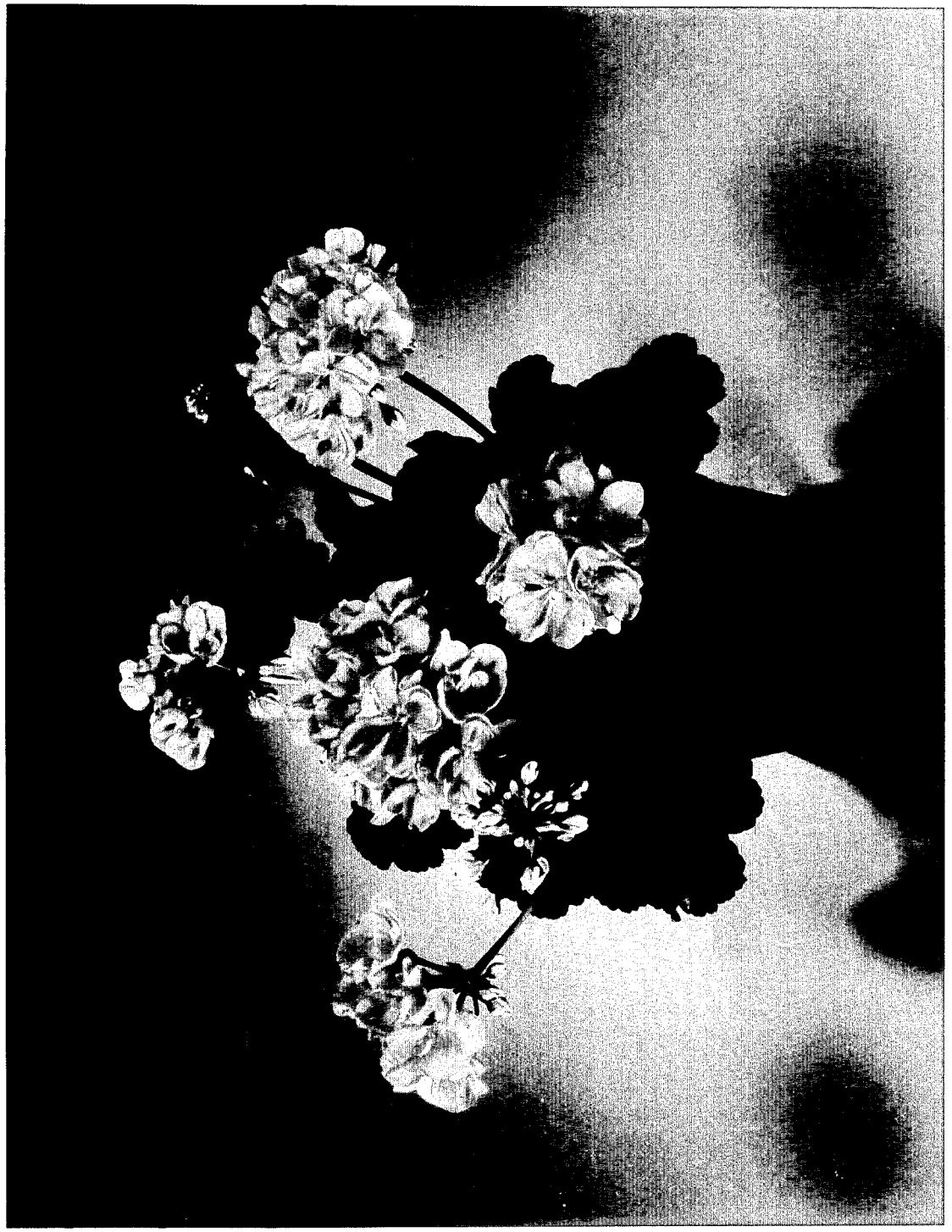

* * * * *